(12) United States Patent
Juestel et al.

(10) Patent No.: US 7,053,542 B2
(45) Date of Patent: May 30, 2006

(54) RARE-GAS LOW-PRESSURE DISCHARGE LAMP, METHOD OF MANUFACTURING A RARE-GAS LOW-PRESSURE DISCHARGE LAMP, AND APPLICATION OF A GAS DISCHARGE LAMP

(75) Inventors: Thomas Juestel, Aachen (DE); Hans Nikol, Aachen (DE); Cornelis Jojakim Jalink, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/914,437

(22) Filed: Aug. 9, 2004

(65) Prior Publication Data

US 2005/0007021 A1    Jan. 13, 2005

Related U.S. Application Data

(63) Continuation of application No. 09/852,166, filed on May 9, 2001, now Pat. No. 6,787,979.

(30) Foreign Application Priority Data

May 13, 2000    (DE)    ............................... 100 23 504

(51) Int. Cl.
   *H01J 61/64*    (2006.01)

(52) U.S. Cl. ........................ 313/485; 313/572

(58) Field of Classification Search ............... 313/484, 313/485; 445/14, 16, 26, 52; 427/58, 64, 427/67
See application file for complete search history.

(56) References Cited

U.S. PATENT DOCUMENTS

| | | | | |
|---|---|---|---|---|
| 3,670,193 | A * | 6/1972 | Thorington et al. | 313/487 |
| 4,233,336 | A * | 11/1980 | Verdult et al. | 427/67 |
| 4,544,997 | A * | 10/1985 | Seuter et al. | 252/301.4 P |
| 4,559,470 | A * | 12/1985 | Murakami et al. | 313/487 |
| 4,576,833 | A * | 3/1986 | Scholten et al. | 427/67 |
| 5,343,114 | A * | 8/1994 | Beneking et al. | 313/485 |
| 5,557,112 | A * | 9/1996 | Csoknyai et al. | 250/504 R |
| 5,604,410 | A * | 2/1997 | Vollkommer et al. | 313/607 |
| 5,811,924 | A * | 9/1998 | Okumura et al. | 313/487 |
| 5,866,984 | A * | 2/1999 | Doughty et al. | 313/485 |
| 6,048,241 | A * | 4/2000 | Traksel et al. | 313/490 |
| 6,304,029 | B1 * | 10/2001 | De Bot et al. | 313/490 |
| 6,417,614 | B1 * | 7/2002 | Ronda et al. | 313/485 |

* cited by examiner

*Primary Examiner*—Ashok Patel

(57) ABSTRACT

A rare-gas low-pressure discharge lamp for generating ultraviolet light, in particular for cosmetic or therapeutic purposes, has a discharge vessel which is filled with rare gas and is at least partly transparent to UV light and which is at least partly coated with a phosphor which radiates UV light upon excitation by an excitation radiation produced in the discharge vessel so as to utilize a desired spectral range.

2 Claims, 4 Drawing Sheets

Figure 1:
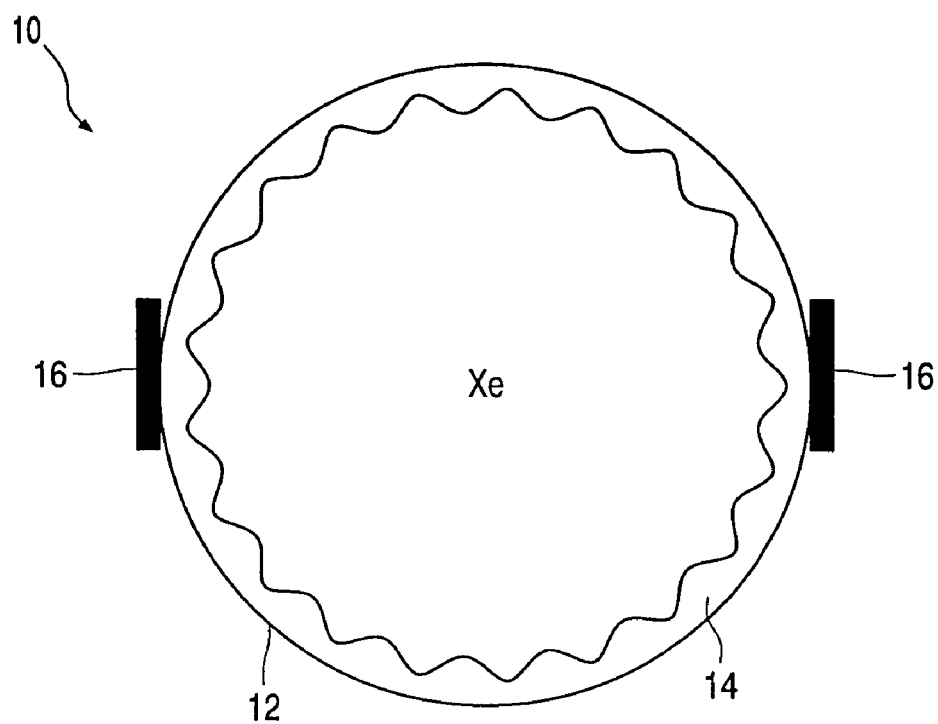

RARE-GAS LOW-PRESSURE DISCHARGE LAMP, METHOD OF MANUFACTURING A RARE-GAS LOW-PRESSURE DISCHARGE LAMP, AND APPLICATION OF A GAS DISCHARGE LAMP

CROSS REFERENCE TO RELATED APPLICATION

This is a continuation of prior application Ser. No. 09/852,166, filed May 9, 2001, which issued Sep. 7, 2004 as U.S. Pat. No. 6,787,979.

The invention relates to a rare-gas low-pressure discharge lamp, a method of manufacturing a rare-gas low-pressure discharge lamp, and various applications of a gas discharge lamp, in particular for cosmetic or therapeutic purposes.

Rare-gas low-pressure discharge lamps are known. They serve, for example, for background lighting of LCD displays. In addition, WO 98/19327 discloses a xenon lamp which generates light with strictly limited spectral lines for certain therapeutic purposes. This lamp, however, is not suitable for wide application ranges, in particular as a suntanning lamp in solariums.

Known suntanning lamps are on the one hand mercury low-pressure gas discharge lamps provided with one or two phosphors, or high-pressure mercury vapor discharge lamps without phosphor. Both types of lamps emit mainly in the UV-A range. It is advantageously possible in the case of lamps with phosphors to adjust the UV-A spectrum by means of the composition of the phosphor, but on the other hand both lamps disadvantageously contain highly toxic mercury, which means that they have to be disposed of with great care.

The suntanning results obtained with these lamps, in particular the skin color and the permanence of the suntanning effect, depend mainly on the spectral power distribution of the UV source, because both reddening of the skin (erythema) and the immediate and delayed pigment formation show a strong dependence on the wavelength of the radiated UV light. Accordingly, an additional UV-B phosphor is added in several lamp types so as to modify the spectrum of the lamps in a desired manner. The spectrum of the lamps is usually identified by means of the following ratios: UV-B/UV-A, UV-$A_1$/UV-$A_2$, and erythema B/erythema A. The quantities usually vary within the following wavelength ranges: UV-$A_1$=340 to 400 nm, UV-$A_2$=320 to 340 nm, erythema B=280 to 320 mm, erythema A=320 to 400 nm, UV-B=280 to 320 nm.

Lamps were developed recently whose phosphor compositions are based on a mixture of $LaPO_4$:Ce (LAP for short) and $BaSi_2O_5$:Pb (BSP). These lamps show an erythema efficiency spectrum which is very similar to that of the sun.

Although major steps forward have been made in the field of suntanning lamps, they still have a number of disadvantages which are directly linked to the use of the mercury plasma. Thus, for example, a few spectral lines of the mercury plasma lie in the UV range (297, 312.5, and 365 nm), and a few lie in the visible range (405, 435, 546, and 579 nm). The presence of these visible mercury lines gives the light of these lamps a bluish appearance, which is not appreciated by the customers. The mercury vapor lines in the UV range in addition interfere with the free adjustability of the UV spectrum by means of the phosphor and are to be taken into account in the calculation of the specification parameters of such a lamp.

A further disadvantage is the low stability of these lamps. Thus, for example, the interaction of the mercury with certain phosphors, for example BSP, leads to a UV-absorbing layer which strongly reduces the UV efficacy during lamp life. In addition, the desired UV light is not immediately available because of the starting behavior of the lamps. Finally, the lamp geometry is limited to tubular shapes, so that a field of lamps arranged next to one another is to be used in order to obtain a suitable light distribution over a larger surface area such as, for example, in a suntanning couch. Even though several lamps are arranged next to one another, a perfectly homogeneous light distribution is never obtained.

The invention accordingly has for its object to provide a lamp of the kind mentioned in the opening paragraph and a method of manufacturing such a lamp which are particularly suitable for cosmetic and therapeutic purposes, rendering it possible to utilize the advantages of a rare-gas low-pressure discharge lamp for generating UV light of a certain spectral range.

This object is achieved by means of a rare-gas low-pressure discharge lamp with a discharge vessel which is filled with a rare gas and is at least partly transparent to UV light, wherein the discharge vessel is at least partly coated with a phosphor which radiates UV light when excited by an excitation light produced in the discharge vessel.

A major advantage of such a lamp is that light of the desired type can be available immediately after ignition, whereas in mercury vapor discharge lamps the mercury is to be evaporated first. A further advantage of the lamp is its very long useful life, usually more than 20,000 hours of operation. In addition, the lamp is environmentally friendly because it does not contain any toxic mercury.

A rare gas such as, for example, xenon or neon emitting exclusively in the VUV and/or UV-C range can be used in the discharge vessel because a UV source with a broadband emission in the range from 290 to 400 nm without additional plasma emission lines in the UV and/or visible range is desired for suntanning purposes. It may also be useful to use a mixture of these two gases. The generated short wavelengths may then be converted into suitable UV-A and/or UV-B light by one phosphor or a mixture of several phosphors. This has the advantage that no plasma lines are in the visible range, so that the light radiated by the lamp is not perceived as unpleasant by the user.

In a preferred embodiment of the invention, the discharge vessel is at least partly made of a glass, preferably of a glass having a transmissivity of 20 to 70% for light of 312.6 nm wavelength.

The invention advantageously enables the manufacture of a lamp in which the spectral power distribution depends only on the phosphor or phosphor mixture used. It was found to be particularly advantageous when a phosphor or a combination or mixture of several phosphors is used in which less than 1% of the light radiated thereby upon excitation by an excitation light produced in the discharge vessel has wavelengths below 290 nm, between 1% and 10% of the radiated light has wavelengths between 290 and 320 nm, and less than 5% of the radiated light has wavelengths above 400 nm.

Such radiation properties allow of the use of, for example, phosphors or combinations of phosphors such as $BaSi_2O_5$:Pb (BSP for short), $CeMgAl_{11}O_{19}$ (CAM), $LaPO_4$:Ce (LAP), $SrB_4O_7$:Eu (SBE), and $(Sr,Ba)MgSi_2O_7$:Pb (SMS). These phosphors have a high efficacy when excited by VUV, in particular in the range from 140 to 190 nm in which the rare-gas discharge lamps mainly emit, and their emission bands lie in the UV-A and/or UV-B range, each with a comparatively small width, so that the emission can be concentrated in one range in which, for example, the suntanning efficacy is particularly high. The use of a combination of a UV-B phosphor, for example LAP, and a UV-A phosphor, for example BSP, renders it possible to adjust the specification parameters of the lamp such that the desired approximation of a given desired spectrum is achieved.

Since the light generated by the lamp should as a rule be radiated in a preferred direction, a UV-light reflecting layer, in particular a layer comprising MgO and/or $Al_2O_3$, may be provided on portions of the discharge vessel so that the high-energy UV light generated in the discharge vessel can be guided to certain portions of the discharge vessel at which it is to be converted into low-energy UV light, such that the lamp has a very high efficacy and a correspondingly high suntanning power.

The lamp according to the invention advantageously enables a completely new, free design of the lamp geometry, in particular in the case of suntanning lamps, which may be, for example, curved or planar, whereas the familiar mercury vapor discharge lamps always had to be tubular in shape. Thus it becomes possible to adapt the discharge vessel to the contours of a surface to be irradiated by the lamp.

In addition, the invention proposes a corresponding manufacturing process for such a lamp. Here, in particular, a suspension of the phosphor to be applied may be prepared and may be provided on the inner side of the discharge vessel. A suitable process for this is preferably a flush coating process, in which case a coating weight lying in a range of 2 to 6 mg/cm$^2$ was found to be advantageous. Subsequently, the suspension is fixed, for example through baking-out of a binder, and the discharge vessel is sealed and filled.

Accordingly, the invention proposes a discharge vessel suitable for this as well as a manufacturing method for such a discharge vessel.

Such a discharge lamp may find its application in particular in a UV-light irradiation device for promoting skin pigmentation or for cosmetic or therapeutic purposes. The invention also relates to the use of a gas discharge lamp as a suntanning lamp, in which a phosphor is excited by light having a wavelength below 200 nm. The use of the radiation which is in itself unsuitable for suntanning purposes and is indeed harmful in direct contact with the skin, surprisingly renders possible a much more flexible choice in the light radiated by the phosphor and thus a suitable, optimized adaptation of the radiated spectrum.

Figure 2:
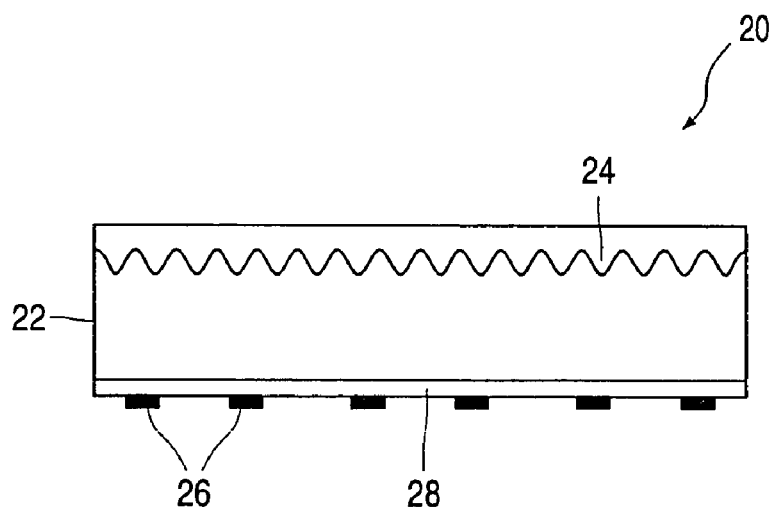
Figure 3:
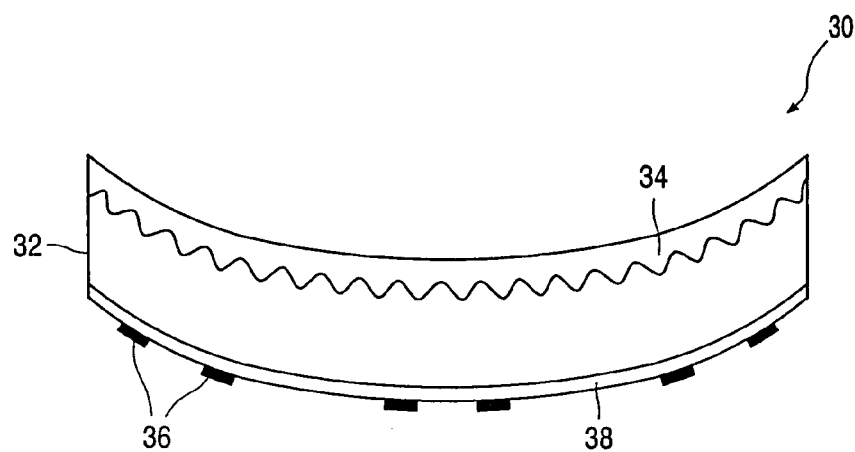
Figure 4:
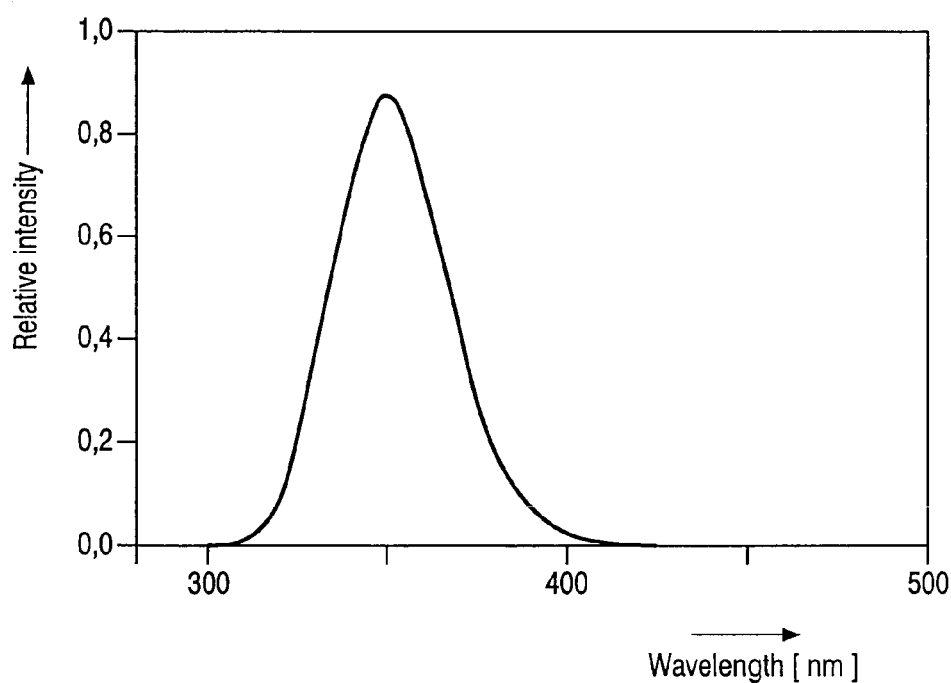
Figure 5:
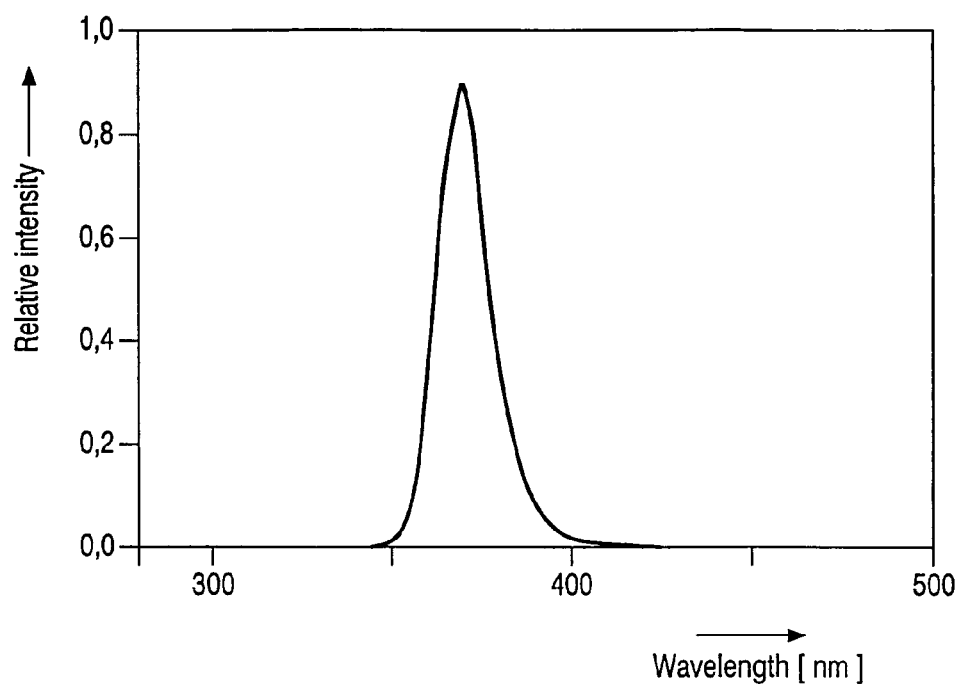
Figure 6:
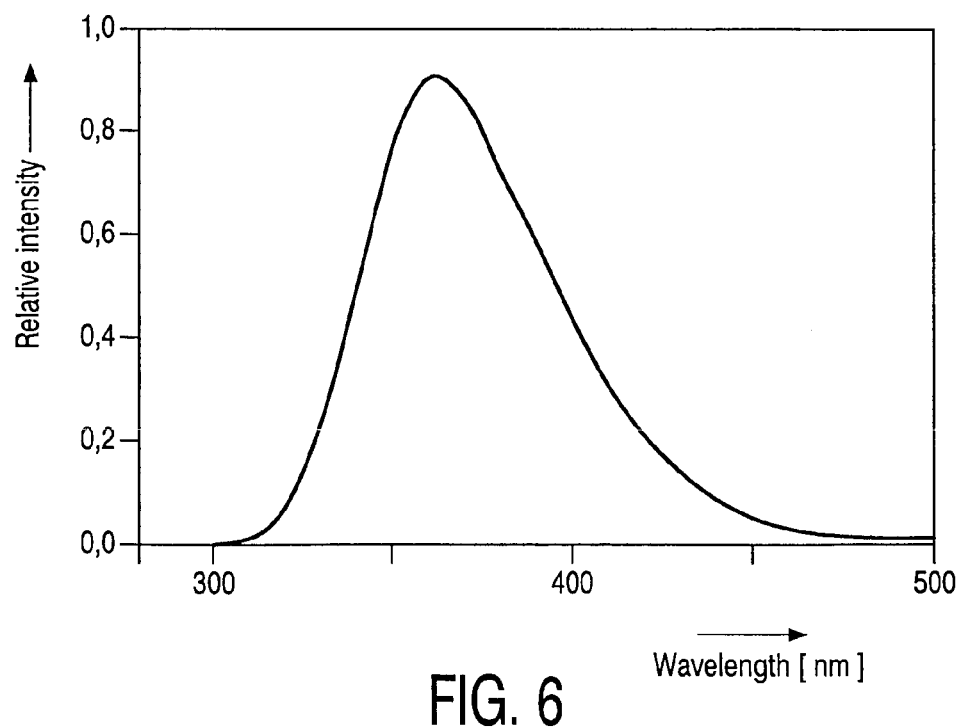
Figure 7:
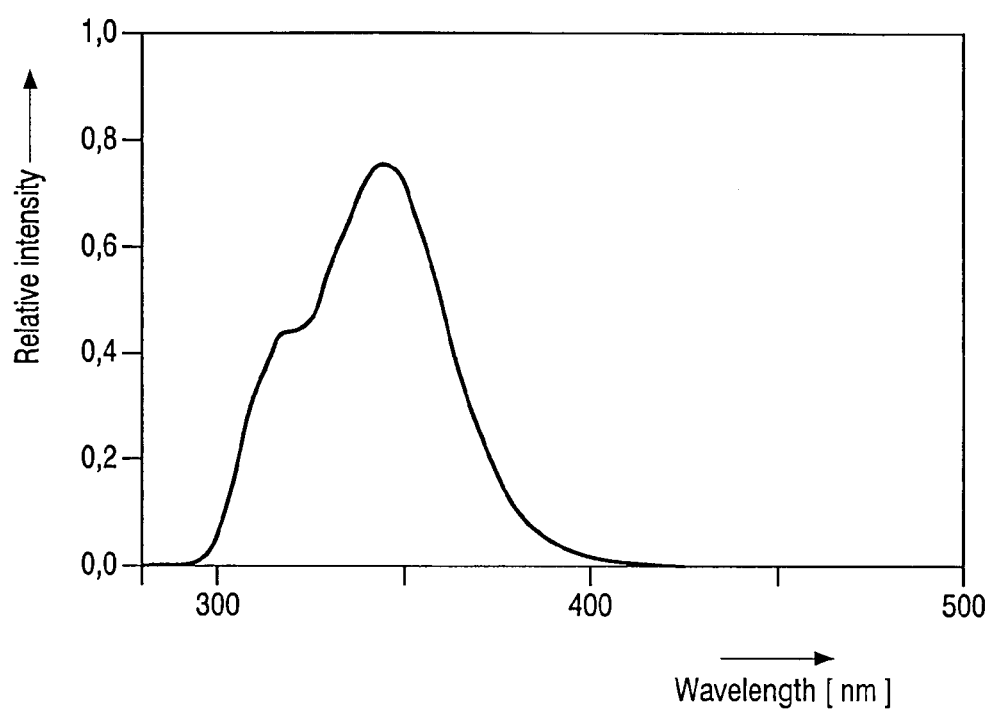

Further particulars, objects, and advantages of the invention will become apparent from the subsequent description of a few embodiments of lamps according to the invention and embodiments of methods according to the invention, all given purely as examples to which the invention is by no means limited, with reference to the drawing, in which:

FIG. 1 is a diagrammatic cross-sectional view of an embodiment of a tubular DBD (dielectric barrier discharge) lamp according to the invention for suntanning purposes with external, strip-type electrodes, FIG. 2 is a diagrammatic cross-sectional view of a planar DBD lamp for suntanning purposes with external strip-type electrodes, FIG. 3 is a diagrammatic cross-sectional view of a curved DBD lamp for suntanning purposes with external, strip-type electrodes, FIG. 4 shows the emission spectrum of a single-component DBD lamp with BSP phosphor in standard glass, FIG. 5 shows the emission spectrum of a single-component DBD lamp with SBE phosphor in standard glass, FIG. 6 shows the emission spectrum of a xenon gas discharge lamp with an SMS phosphor, and FIG. 7 shows the emission spectrum of a xenon gas discharge lamp with a phosphor mixture of 40% LAP and 60% BSP.

In FIG. 1, a rare-gas low-pressure discharge lamp referenced 10 in its totality with a dielectric barrier layer is shown, the emission maximum of the lamp lying in the UV-A range. The lamp comprises a gastight discharge vessel 12 which in this embodiment is tubular in shape and filled with xenon. The discharge vessel 12 is provided with a luminescent layer 14 all over its inner side, which layer comprises at least one luminescent material which emits in the UV-A range (320–400 nm). An additional luminescent material emitting in the UV-B range (280–320 nm) may be added so as to adjust the UV-B/UV-A ratio.

Two electrodes 16, for example Al electrodes or so-called ITO electrodes (ITO=indium tin oxide=$SnO_2$:In), are provided on the outer side of the discharge vessel 12, said ITO electrodes having the advantage that they are transparent. The so-called DBD (dielectric barrier discharge) lamp thus constructed has a high power density and a long operational life which may be more than 20,000 hours.

The plasma emission spectrum of this lamp covers a narrow emission band whose center lies at 172 nm when filled with xenon, only a few lines of low intensity being emitted in the infrared region at approximately 828 nm. The UV emission spectrum of the lamp now advantageously depends on the choice of the UV-A and UV-B phosphors. In addition, such a lamp provides a 100% power output in the VUV range (140 to 190 nm) within a few milliseconds.

Since the lamp type is not limited to a given, in particular tubular shape, it is also possible to manufacture lamps with a planar or curved geometry, as is shown in FIGS. 2 and 3. This lamp type accordingly renders it possible to manufacture, for example, suntanning couches with a very homogeneous light distribution.

FIGS. 2 and 3 are diagrammatic cross-sectional views of a planar DBD lamp 20 (FIG. 2) and a curved DBD lamp 30 (FIG. 3), respectively. The two lamps each have a respective discharge vessel 22, 32 which is filled with rare gas and is partly coated at its inner side, i.e. in the region of the desired radiation direction, with a phosphor or a phosphor combination 24, 34, as desired, for converting the high-energy UV light generated in the discharge vessel during lamp operation into low-energy UV light.

Strip-shaped electrodes 26 and 36 are provided on the outside of the respective discharge vessels.

To increase the efficiency of the lamps, a UV reflector 28, 38 is provided on each of the two lamps on the side of the discharge vessel opposed to the desired radiation direction. Such a UV reflector may be realized in various ways and be optimized to suit the respective application, for example through the provision of a coating on the discharge vessel, or in the form of a separate UV reflection mirror.

An example of the manufacture of a single-component DBD lamp with BSP phosphor in standard glass with a transmission $T_{312.6\ nm}$ of 35% for light of a wavelength of 312.6 nm will now be given below.

A suspension of BSP in butyl acetate with nitrocellulose as a binder is prepared. The suspension is provided on the inner side of a discharge vessel in the form of a lamp tube of standard glass of 1 mm thickness in a flush coating process, which leads to a 35% transmission of light with a wavelength of 312.6 nm for a typical coating weight of the phosphor layer of 2 to 6 mg/cm$^2$.

The binder is baked out in a heating cycle with top temperatures between 500 and 600° C. The glass tube is sealed and filled with xenon. The gas pressure of the xenon should lie between 200 and 300 mbar. Al electrodes are provided on the outer side of the lamp through adhesion or dipping.

Such a lamp can then be operated with a square-wave AC voltage of 6 kV and 25 kHz. The emission spectrum of such a lamp is shown in FIG. 4, while FIGS. 5, 6, and 7 show the emission spectrums of a single-component DBD lamp with SBE phosphor in standard glass (FIG. 5), a xenon gas discharge lamp with an SMS phosphor (FIG. 6), and a xenon gas discharge lamp on whose discharge vessel a mixture of 40% LAP and 60% BSP phosphor was provided (FIG. 7). The methods of manufacturing these lamps all correspond to the method described above.

The invention claimed is:

1. A method of manufacturing a mercury-free rare-gas low-pressure discharge lamp for generating ultraviolet light, in particular for cosmetic or therapeutic purposes, with a discharge vessel filled with rare gas and at least partly transparent to UV light, characterized in that the discharge vessel is at least partly coated with a phosphor which radiates UV light when excited by excitation radiation produced in the discharge vessel.

2. A method as claimed in claim 1, characterized in that
   a suspension of the phosphor to be applied is prepared on the basis of butyl acetate with nitrocellulose as a binder,
   the suspension is provided on the inner side of the discharge vessel in a flush coating process so as to have a coating weight of between 2 and 6 mg/cm$^2$,
   the binder is baked out in a heating cycle with top temperatures between 500 and 600° C.,
   the discharge vessel is sealed and filled with rare gas, in particular with xenon or neon with a pressure of between 200 and 300 mbar, and
   electrodes are applied to the outer side of the discharge vessel.

* * * * *